US005161542A

United States Patent [19]
Palestrant

[11] Patent Number: 5,161,542
[45] Date of Patent: Nov. 10, 1992

[54] METHOD FOR ACQUIRING SOFT TISSUE BIOPSY SPECIMENS

[76] Inventor: Aubrey Palestrant, 6800 N. 47th St., Paradise Valley, Ariz. 85253

[21] Appl. No.: 807,270

[22] Filed: Dec. 13, 1991

Related U.S. Application Data

[62] Division of Ser. No. 572,055, Aug. 23, 1990, Pat. No. 5,090,419.

[51] Int. Cl.⁵ ............................................. A61B 10/00
[52] U.S. Cl. ................................................... 128/754
[58] Field of Search ........................ 128/749, 751–754; 606/167, 170, 171

[56] References Cited

U.S. PATENT DOCUMENTS

| | | | |
|---|---|---|---|
| 4,699,154 | 10/1987 | Lindgren | 128/754 |
| 4,732,215 | 4/1988 | Goto et al. | 128/754 |
| 4,924,878 | 5/1990 | Nottle | 128/751 |
| 4,958,625 | 9/1990 | Bates et al. | 128/754 |

OTHER PUBLICATIONS

Becton et al. "Biopsy Needles & Instruments For Advanced Techniques" Becton, Dickson & Co. Pamphlet 12 pgs, Oct. 1974.
Gazelle et al., "Guided Percutaneous Biopsy of Intra abdominal Lesions", *AJR* 153: 929–935, Nov. 1989.
Brochure entitled "Medi-Tech ASAP Biopsy System", published by Boston Scientific Corporation, of Watertown, Mass., believed to have been printed in Feb. 1990.
Brochure entitled "Microinvasive ASAP 18 Automatic Biopsy System", published by Boston Scientific Corporation, of Watertown, Mass., believed to have been printed in Sep. 1989.
Pamphlet entitled "Bard Biopty Instrument Biopty-Cut Needle", believed to have been published by Bard Urological Division of C. R. Bard, Inc. of Covington, Ga., on or about Sep. 1987.
Parker et al., "Technical Note; Adaptation of the Bard Prostate Biopsy Gun for CT-Guideed Abdominal Biopsies", *Cardio Vascular and Interventional Radiology*, (1989) 12: 50–52.
Parker et al., "Image-directed Percutaneous Biopsies with a Biopsy Gun", *Radiology*, June 1989; 171: 663–669.
Cook Urological Incorporated brochure entitled "Roth Spiral Rotating Biopsy Needle", published by Cook Urological Incorporated of Spencer, Ind., bearing a 1986 copyright notice.
Brochure entitled "Tru-Cut Biopsy Needles" published by Travenol Laboratories, Inc. of Deerfield, Ill., dated Nov. 1980.
Pages 3–5, "Biopsy Needles and Brushes", from unidentified medical supply catalog, of unknown date.

*Primary Examiner*—Max Hindenburg
*Attorney, Agent, or Firm*—Cahill, Sutton & Thomas

[57] ABSTRACT

An apparatus and method for acquiring biopsy specimens includes an outer cannula having a bevelled distal end and an opposing proximal end having a Luer-type fitting. A stylet having a like bevelled distal end is inserted within the outer cannula before the cannula is placed within the patient. Following placement of the outer cannula, the stylet is removed, and a biopsy actuator equipped with a biopsy needle is then inserted within the proximal end of the cannula. The distal tip of the biopsy needle is provided with a specimen retaining notch. The biopsy actuator includes a mating Luer-type fitting that is releasably attached to the proximal end of the cannula. The biopsy actuator includes a spring-loaded trigger mechanism for advancing the distal end of the biopsy needle to expose the specimen retaining notch, and thereafter rapidly advances the distal end of the cannula to cut tissue prolapsed within the notch. The Luer fittings are then disengaged, the biopsy actuator is withdrawn, and a second specimen may then be taken by inserting a second biopsy actuator in a like manner.

5 Claims, 2 Drawing Sheets

U.S. Patent    Nov. 10, 1992    Sheet 1 of 2    5,161,542
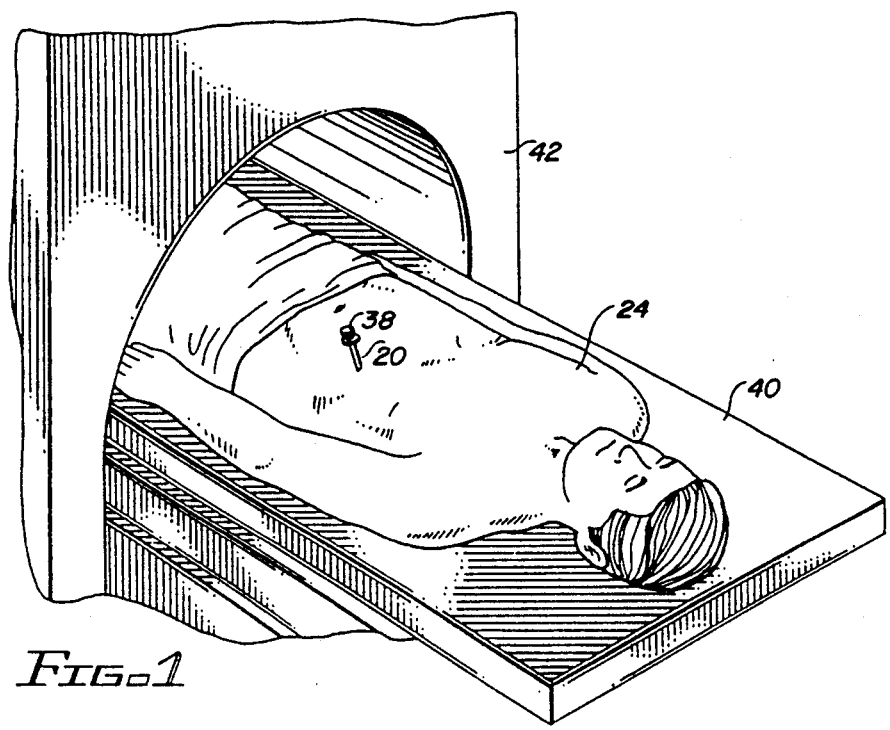
FIG.1
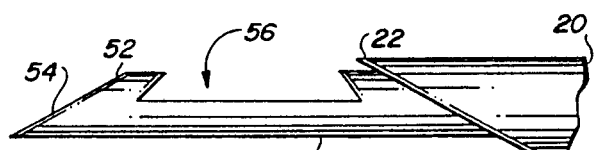
FIG.5
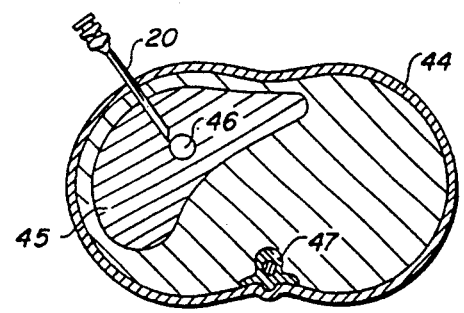
FIG.2
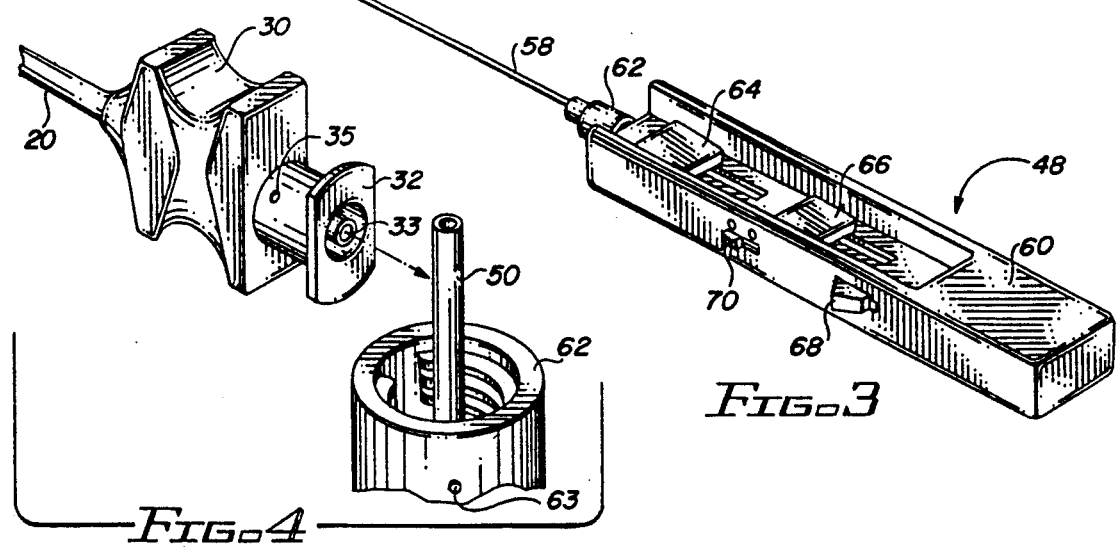
FIG.3
FIG.4

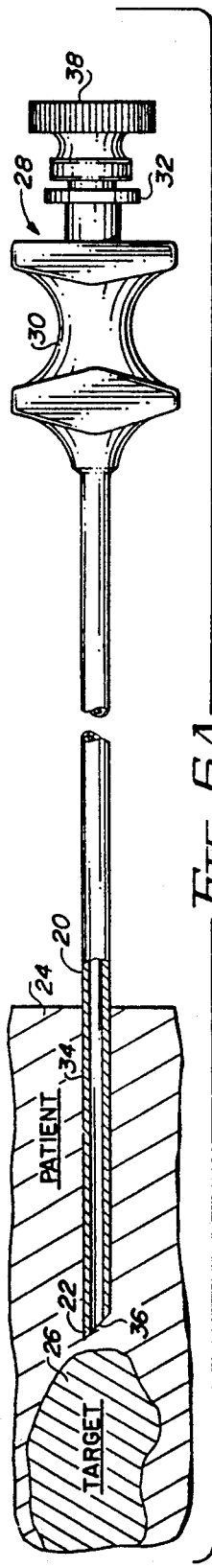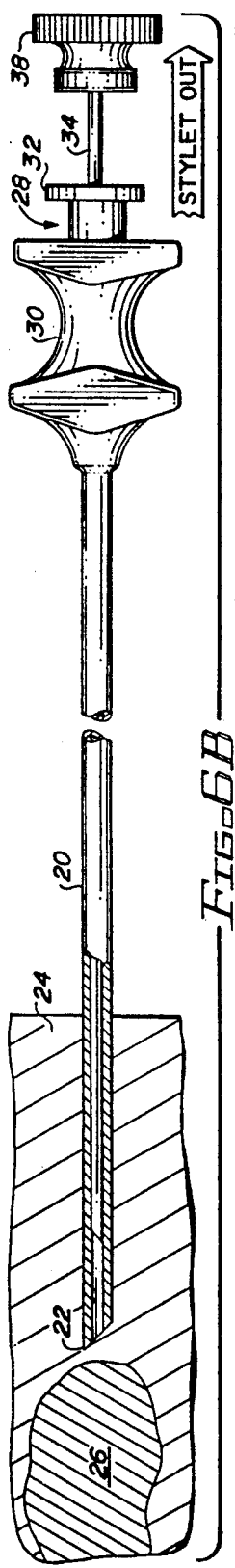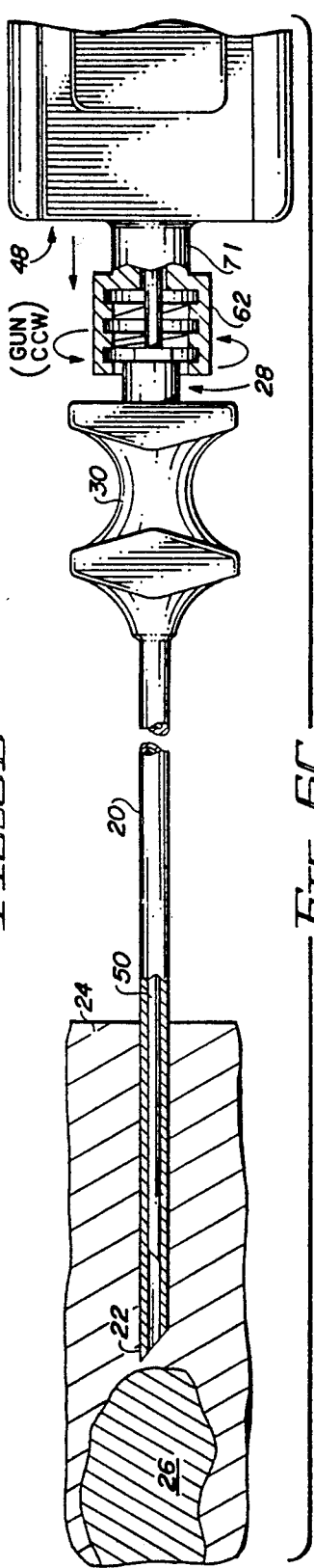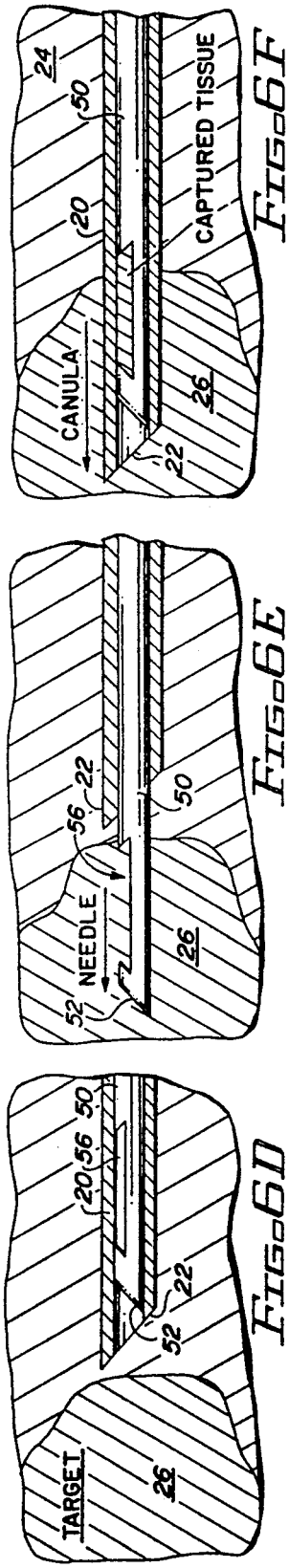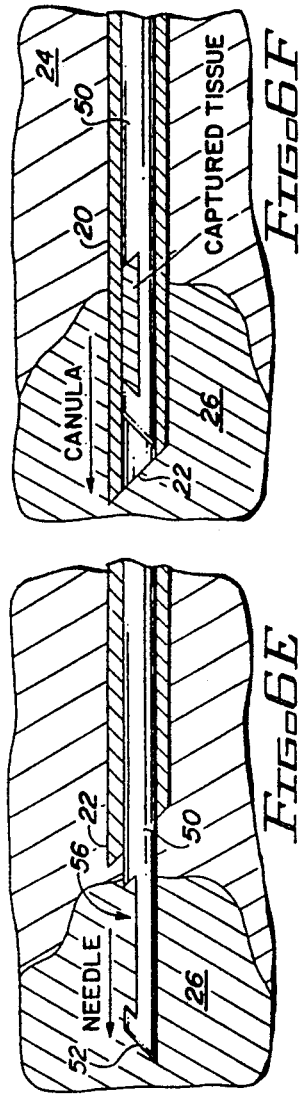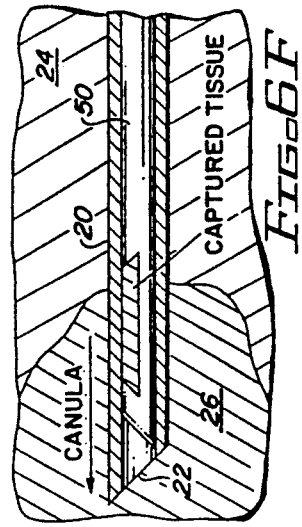

METHOD FOR ACQUIRING SOFT TISSUE BIOPSY SPECIMENS

CROSS-REFERENCE TO RELATED APPLICATIONS

The present application is a division of copending U.S. patent application Ser. No. 07/572,055, filed by the present applicant on Aug. 23, 1990, now U.S. Pat. No. 5,090,419, and the benefit of the original filing date of such earlier application is claimed herein.

BACKGROUND OF THE INVENTION

1. Field of the Invention

The present invention relates generally to medical cannulas and stylets used to obtain soft tissue biopsy specimens, and more specifically, to an apparatus and method for acquiring multiple biopsy specimens from a selected target tissue while requiring only a single cannula placement in a manner which may be confirmed using CT scanning or other imaging techniques.

2. Description of the Prior Art

Biopsy of abnormal tissues in animals and humans for diagnosis is a common procedure. Many forms of biopsy apparatus are known; typically, such apparatus includes an outer cannula having a distal end and adapted to slidingly receive a stylet or needle. The biopsy needle or stylet typically occludes the distal end of the cannula to prevent tissue coring as the cannula is advanced into the patient. The stylet or biopsy needle also typically includes a specimen retaining notch which is covered by the outer cannula as the cannula is advanced into the patient toward the target organ or target tissue mass. Once the outer cannula is positioned in the target organ or tissue mass, the distal end of the stylet is advanced relative to the distal end of the cannula for exposing the specimen retaining notch and allowing tissue proximate thereto to prolapse within the specimen retaining notch. Thereafter, the distal end of the outer cannula is further advanced to slide over the specimen retaining notch to simultaneously cut the tissue prolapsed within the specimen retaining notch and to retain such specimen therein. The specimen may then be removed for analysis, either by simultaneously withdrawing both the outer cannula and inner biopsy needle, or by withdrawing only the biopsy needle while leaving the outer cannula in place. The latter option is preferred in those instances when either multiple specimens, or specimens taken from multiple depths, are required or preferred.

In Gazelle et al., "Guided Percutaneous Biopsy of Intra abdominal Lesions", *AJR* 153: 929-935, November 1989, the authors describe methods for performing multiple pass biopsies; one such method is the double-needle (short cannula coaxial) method wherein a larger-caliber short needle is placed through the skin to serve as a guidance cannula; once its direction is confirmed, a small needle is moved coaxially through the larger needle to the lesion. Multiple passes are performed by leaving the guidance cannula in place and repeating the insertion of the smaller needle.

While manually-operated biopsy devices for cutting tissue specimens are known, they are often difficult to manipulate, particularly since the physician or technician must manipulate the cannula and the inner stylet or needle in proper timed sequence to reliably capture a tissue specimen. Moreover, it is preferred that the distal tip of the cannula be rapidly advanced over the specimen retaining notch, both to avoid dislodging the tissue prolapsed within the specimen retaining notch, and to avoid crushing the tissue specimen disposed therein.

In an effort to automate and/or mechanize the above-described biopsy procedure. Spring-loaded biopsy systems have been developed and made available for automating the timed sequence of manipulating the outer cannula and biopsy needle to obtain a tissue specimen. For example, Boston Scientific Corporation of Watertown, Mass. has made commercially available a mechanized biopsy system under the trademark "MEDI-TECH ASAP BIOPSY SYSTEM" wherein a stylet and surrounding cannula extend from a plastic handle. Thumb tabs are provided for the user to retract both the stylet and the surrounding cannula, whereby the specimen retaining notch of the stylet is covered by the cannula. After inserting the distal tip of the instrument at the edge of the region to be sampled, a trigger disposed on the handle unit is activated to sequentially advance first the stylet to automatically expose the specimen retaining notch and thereafter slide the distal end of the outer cannula thereover to sever and retain the tissue specimen.

Similarly, a one-handed, single-use, soft tissue biopsy cutting device is commercially available from The Perry Group, Ltd. of St. Louis, Mo. under the trademark "KLEAR KUT".

Within U.S. Pat. No. 4,699,154 issued to Lindgren, a tissue sampling device is disclosed for obtaining biopsy specimens wherein propelling springs are provided to sequentially advance an inner needle and an outer needle for capturing a tissue sample. A release button or trigger is provided upon the spring housing for triggering the timed sequence of the inner and outer needles.

A device substantially similar to that disclosed in the above-noted patent to Lindgren is commercially available from the Bard Urological Division of C.R. Bard, Inc. of Covington, Ga., under the registered trademark "BIOPTY". While sold to perform a biopsy of the prostate, the "BIOPTY" gun and related "BIOPTY-CUT" needle have also been proposed for performing CT-guided abdominal biopsies. See Parker et al., "Technical Note: Adaptation of the Bard Prostate Biopsy Gun for CT-Guided Abdominal Biopsies", *CardioVascular and Interventional Radiology*, (1989) 12: 50–52; and Parker et al., "Image-directed Percutaneous Biopsies with a Biopsy Gun", *Radiology*, June 1989; 171: 663–669. The BIOPTY-CUT 18-gauge needle is not adapted to be used apart from the BIOPTY gun, but needle placement is more cumbersome when the gun is attached. Parker et al. describe a technique of placing the BIOPTY-CUT needle within the body before attachment of the needle to the gun. A short section of sterile plastic sheath is inserted around the cutting needle between the hub of the cannula and the hub of the cutting needle to maintain the two in fixed relationship; following placement of the BIOPTY-CUT needle, the needle is "pinned" to the skin before the gun is attached to avoid displacement of the needle tip longitudinally or introduction of unwanted angulation. The short section of plastic sheath is removed, and the needle hub assembly is then inserted into the spring-loaded sleds of the BIOPTY biopsy gun.

However, the "MEDI-TECH" biopsy system, "KLEAR KUT", biopsy system, the tissue sampling device disclosed by Lindgren, and the BIOPTY biopsy system are all single-use devices, i.e., the outer cannula and inner stylet or needle are both removed as a unit after a specimen is obtained. To remove the tissue specimen trapped within the specimen retaining notch, the entire device, including the outer cannula, is withdrawn from the patient. However, the pathologist who must analyze such tissue specimens often prefers that multiple specimens be obtained, for example, at varying depths along the insertion tract. In such instances, the aforementioned mechanized biopsy systems must be repeatedly inserted and withdrawn to acquire such multiple specimens.

In U.S. Pat. No. 4,735,215, issued to Goto et al., a related mechanized biopsy instrument is disclosed. The biopsy instrument disclosed by Goto et al. differs in at least two respects from the mechanized biopsy instruments described above. First, the stylet of the instrument is not advanced by a spring-loaded mechanism; rather, the housing assembly of the device disclosed by Goto et al. includes a mechanism for retracting and subsequently advancing the outer cannula to first expose and then cover the specimen notch provided within the stylet. Secondly, the housing manipulated by the user is broken into two releasable halves, allowing the stylet to be withdrawn from the cannula without removing the cannula from the patient to facilitate the taking of multiple specimens.

However, all of the mechanized devices and instruments described above tend to be bulky and heavy. When the target tissue lies deep within patient, some form of imaging is commonly employed to direct the distal end of the biopsy system to the desired target. Such imaging techniques may include fluoroscopic, ultrasound, CT scanning, or MRI equipment. If fluoroscopy is used, the large handle associated with mechanized biopsy guns may obscure visualization of the target and needle tip. When performing a CT guided biopsy procedure, the physician must check the progress of the biopsy instrument intermittently while it is advanced toward the target. Such CT guided procedures require the physician to release his or her grip on the biopsy instrument to allow the patient to be transported through the scanner for imaging. However, the bulk of the mechanized biopsy instruments described above does not allow scanning to occur because the patient and the biopsy instrument cannot both fit into the scanning aperture Moreover, the weight of the handle housing for such devices is significantly great to deflect the outer cannula during scanning; therefore, the image that is obtained may not be an accurate indication of the direction of passage. The metal housing associated with some biopsy guns may degrade the CT scanned image by causing major artifacts, thereby limiting the physician's ability to see the position of the needle in the patient.

Even with respect to the aforementioned BIOPTY-CUT needle placement method described by Parker et al. for use with the BIOPTY biopsy gun, the authors state that the length of the BIOPTY-CUT needle poses gantry clearance problems during CT scanning, and they further state that the act of attaching the gun to the needle after localization can be awkward. Moreover, as already noted, Parker et al. state that the BIOPTY-CUT needle must be "pinned" to the skin before reattachment to the gun.

Accordingly, it is an object of the present invention to provide an apparatus and a method for acquiring biopsy specimens wherein the outer cannula and inner biopsy needle may be easily manipulated in timed sequence using an automatic, mechanized instrument or actuator.

It is another object of the present invention to provide such an apparatus and method wherein the proper placement of the outer cannula relative to the target tissue may easily be verified using CT guided scanning techniques or other imaging modalities.

It is still another object of the present invention to provide such an apparatus and method wherein multiple tissue specimens and/or tissue specimens from multiple depths along the same insertion tract, may be acquired without requiring the withdrawal of the outer cannula between successive specimens.

These and other objects of the present invention will become more apparent to those skilled in the art as the description thereof proceeds.

SUMMARY OF THE INVENTION

Briefly described, and in accordance with one embodiment thereof, the present invention relates to an apparatus for acquiring biopsy specimens and including an outer cannula having a distal end for insertion into a patient and including an opposing proximal end having a first connector, such as a Luer-lock type fitting, secured thereto. The apparatus includes a stylet adapted to slide within the outer cannula through the proximal end thereof for closing the distal end of the outer cannula. The apparatus further includes a biopsy actuator having an elongated biopsy needle extending therefrom. The biopsy needle is adapted to slide within the outer cannula following removal of the aforementioned stylet. The biopsy needle includes a distal end having a specimen retaining notch formed therein for retaining a biopsy specimen.

The biopsy actuator further includes a second connector, preferably a Luer-lock type fitting, for releasably coupling the biopsy actuator to the first connector secured to the proximal end of the outer cannula, after the biopsy needle is fully inserted within the outer cannula. The biopsy actuator also includes a trigger mechanism for sequentially exposing the specimen retaining notch of the biopsy needle to allow the target tissue to prolapse within the specimen retaining notch, and thereafter rapidly advance the distal end of the outer cannula over the specimen retaining notch to cut the prolapsed specimen tissue and trap the same within the specimen retaining notch. Preferably, the biopsy needle is permanently secured to the trigger mechanism to form a disposable unit.

The distal end of the outer cannula is preferably bevelled, both to facilitate the insertion of the cannula into the patient, as well as to facilitate cutting of the tissue specimen when the trigger mechanism is operated.

As mentioned above, the first and second mating connectors are preferably Luer-lock type fittings commonly used in conjunction with surgical devices. The biopsy needle extending from the actuator preferably extends through the Luer-lock fitting that releasably engages the corresponding Luer-lock fitting provided on the proximal end of the outer cannula.

Once the outer cannula and biopsy actuator are coupled with each other, the mechanized operation of the apparatus can be performed in essentially two different ways. In one embodiment, the biopsy actuator may cause the outer cannula to retract while causing the biopsy needle to remain stationary, thereby exposing the specimen retaining notch. Alternately, the biopsy actuator may initially cause the distal tip of the biopsy needle to be advanced relative to the distal end of the outer cannula, and thereby expose the specimen retaining notch. In either case, the biopsy actuator subsequently rapidly advances the distal end of the outer cannula over the specimen retaining notch to cut the tissue specimen which has prolapsed within such notch.

The present invention also relates to an improved method for acquiring biopsy specimens, such method including the initial step of inserting a stylet into an outer cannula through a proximal end of the outer cannula to close the distal end thereof. The distal end of the outer cannula, together with the stylet disposed therein, is then inserted into a patient and is directed toward the target tissue mass to be biopsied. The stylet is then removed from the outer cannula, and the biopsy needle extending from the aforementioned biopsy actuator is then inserted within the outer cannula through the proximal end thereof until the distal tip of the biopsy needle is proximate the distal end of the outer cannula. The proximal end of the outer cannula is then coupled to the biopsy actuator, as by mating Luer-lock fittings. The biopsy actuator is then triggered to expose the specimen retaining notch of the biopsy needle, thereafter sliding the distal end of the outer cannula over the specimen retaining notch. The proximal end of the outer cannula is then uncoupled from the biopsy actuator, and the biopsy needle is withdrawn from the proximal end of the outer cannula while the outer cannula remains inserted within the patient. A second tissue specimen may then be obtained by re-inserting the biopsy needle into the outer cannula and again coupling the biopsy actuator to the proximal end of the outer cannula.

Preferably, the aforementioned method includes the step of performing a CT scan after the outer cannula and associated stylet are inserted within the patient to confirm that the distal end of the outer cannula is within or closely proximate the target tissue mass.

BRIEF DESCRIPTION OF THE DRAWINGS

FIG. 1 is a perspective view of a patient positioned upon a CT scanning table and illustrating the manner in which a CT scan may be performed to confirm proper placement of an outer cannula and the associated stylet of a biopsy device.

FIG. 2 is an illustration of an image which might be observed using CT scanning equipment to confirm proper placement of a biopsy instrument within the patient's body.

FIG. 3 is a perspective view of a biopsy actuator and biopsy needle extending therefrom in accordance with the teachings of the present invention.

FIG. 4 is a perspective view of the proximal end and of a mating Luer-lock type fitting provided upon the biopsy actuator.

FIG. 5 is an enlarged side view of the tip of the biopsy needle and the tip of the outer cannula.

FIG. 6A is a cross-sectional view illustrating the insertion of the distal ends of the outer cannula and associated stylet adjacent a target tissue mass.

FIG. 6B is a further cross-sectional drawing corresponding to that shown in FIG. 6A, but wherein the stylet is being withdrawn from the outer cannula.

FIG. 6C is a further cross-sectional drawing corresponding to that shown in FIG. 6A, but wherein a biopsy needle extending from the biopsy actuator has been inserted through the proximal end of the outer cannula and wherein the proximal end of the outer cannula is coupled with the biopsy actuator.

FIG. 6D is an enlarged cross-sectional drawing showing the distal end of the outer cannula and distal tip of the biopsy needle before the biopsy actuator is triggered.

FIG. 6E is a cross-sectional drawing corresponding to that shown in FIG. 6D and indicating the exposure of a specimen retaining notch within the biopsy needle shortly after the biopsy actuator is triggered.

FIG. 6F is a cross-sectional drawing corresponding to those shown in FIGS. 6D and 6E, but indicating that the distal end of the outer cannula has been advanced over the specimen retaining notch of the biopsy needle, and indicating the tissue specimen therein.

DETAILED DESCRIPTION OF THE PREFERRED EMBODIMENTS

In accordance with the present invention, an outer cannula is provided like that designated by reference numeral 20 within FIG. 6A. Outer cannula 20 is preferably a cylindrical tube of approximately 18 gauge made of surgical stainless steel and includes a distal end designated by reference numeral 22, for insertion into a patient's body. Within FIG. 6A, the patient's body is designated by reference numeral 24, and the target tissue mass or organ to be biopsied is designated by reference numeral 26. Outer cannula 20 includes an opposing proximal end designated by reference numeral 28 which may include a handle portion 30 for being grasped between the fingers of a surgeon as the outer cannula 20 is advanced toward target tissue 26. Proximal end 28 of outer cannula 20 further includes a first connector 32, which is preferably a female Luer-lock type fitting commonly used in conjunction with surgical devices.

Still referring to FIG. 6A, an elongated stylet 34 is shown inserted within outer cannula 20. Stylet 34 includes a closed distal end 36 for closing distal end 22 of outer cannula 20 to prevent coring of body tissue as outer cannula 20 is advanced into patient's body 24. As shown in FIG. 6A, stylet 34 includes a handle portion 38 at the proximal end opposing distal end 36 of stylet 34. Stylet 34 is also preferably made of surgical stainless steel.

Still referring to FIG. 6A, outer cannula 20 has a predetermined inner diameter, while stylet 34 has a predetermined outer diameter commensurate therewith, thereby adapting stylet 34 to slide within outer cannula 20 through proximal end 28 thereof. Preferably, both the distal end 22 of outer cannula 20 and the distal end 36 of stylet 34 have corresponding bevels to present a smooth beveled tip during insertion of outer cannula 20 into patient's body 24. The beveled distal tip 22 of outer cannula 20 further facilitates cutting of the tissue specimen after stylet 34 is removed, in a manner explained below. Preferably, means are provided, such as an alignment tab, or Luer-lock fitting upon handle 38 of stylet 20 to insure that the bevel on distal tip 36 is aligned with the bevel on distal tip 22 of outer cannula 20.

Referring to FIG. 1, outer cannula 20 is shown partially inserted within the patient's body 24. As shown in FIG. 1, the patient is lying upon a CT scanning table 40. CT scanning table 40 may be transported within CT scanning gantry 42 to create a CT scanned image, like that shown in FIG. 2. Within FIG. 2, the cross-sectional image designated by reference numeral 44 is a cross-section of patient's body 24 (see FIG. 1), wherein liver 45 and spine 47 are indicated. Within FIG. 2, cannula 20 is visible within the scanned image, while reference numeral 46 designates the target tissue mass within liver 45. Thus, such CT scanning images may be used by a physician to confirm that cannula 20 and associated stylet 34 are being properly directed toward the intended target tissue mass 46. As noted above, apart from the placement method described by Parker et al., mechanized biopsy systems that are presently known include spring-loaded handles or actuators which are relatively bulky and heavy and which would not facilitate the use of CT scanning images to confirm proper placement of the biopsy instrument.

Once the physician has determined that the distal end 22 of outer cannula 20 lies properly adjacent the target tissue mass 26, the physician pulls upon handle 38 of stylet 34, as shown in FIG. 6B to remove the stylet therefrom.

Shown in FIG. 3 is a biopsy actuator 48 which includes a biopsy needle 50 extending therefrom. Biopsy needle 50 is preferably made of surgical stainless steel and includes a distal tip 52, shown in greater detail in FIG. 5. As shown in FIG. 5, distal tip 52 includes a forward most bevelled edge 54 to facilitate passage through tissue, as well as a specimen retaining notch 56 which may be approximately 17 millimeters in length. Biopsy needle 50 has a predetermined outer diameter commensurate with the predetermined inner diameter of outer cannula 20 for adapting biopsy needle 50 to slide within outer cannula 20 through the proximal end 28 thereof after stylet 34 is removed therefrom. As shown in FIG. 5, the tip of distal end 22 of outer cannula 20 is preferably aligned with specimen retaining notch 56 to cleanly cut a tissue sample prolapsed therein. The opposing proximal end 58 of biopsy needle 50 extends within a housing 60 of biopsy actuator 48, which housing further serves as a handle for the biopsy actuator.

While biopsy needle 50 shown in FIG. 5 includes a so-called "Tru-Cut" form of specimen retaining notch 56, other types of specimen retaining biopsy needles may also be used. For example, biopsy needles known as "Vim-Silverman" type needles are adopted to retain a core of a tissue specimen within the distal end of a longitudinally split inner cannula as the outer cannula is advanced thereover. As used herein, the term "specimen retaining notch" should be understood to refer to the specimen retaining portion of any biopsy needle.

Referring jointly to FIGS. 3 and 4, biopsy actuator 48 also includes a connector 62 through which biopsy needle 50 extends. Connector 62 may be retracted toward housing 60 and may alternately be rapidly advanced in a direction away from housing 60. Similarly, biopsy needle 50 may be retracted a short distance within housing 60 and may thereafter be advanced by the same short distance away from housing 60. A pair of thumb tabs 64 and 66 are provided upon biopsy actuator housing 60. A physician may retract biopsy needle 50 by pulling back on thumb tab 66, and may retract connector 62 by pulling back on thumb tab 64. Biopsy actuator housing 60 further includes a trigger switch 68 and a safety switch 70. As will be explained in greater detail below, pulling back on trigger switch 68 actuates the device for obtaining a tissue specimen, while safety switch 70 prevents accidental firing until the physician is ready to trigger the biopsy instrument. Preferably, biopsy needle 50 is permanently secured to biopsy actuator housing 60 and the trigger mechanism housed therein to form an integral, disposable unit.

As indicated above, connector 62 is preferably a male Luer-lock type fitting adapted to releasably connect to female Luer-lock fitting 32 of outer cannula 20, as shown in FIG. 4. As is known to those skilled in the art, Luer-lock fittings of this type are easily coupled by pressing such fittings together and rotating one of the fittings approximately one quarter turn relative to the other. Such Luer-lock fittings may easily be uncoupled from one another by reversing this procedure. As shown in FIG. 4, Luer-lock fitting 32 preferably includes a tubular extension 33 continuous with the lumen within outer cannula 20; tubular extension 33 ensures that the captured specimen is not dislodged from the biopsy needle 50 as tip 52 thereof is withdrawn from Luer-lock fitting 32. As further shown in FIG. 4, alignment markers, in the form of dots 35 and 63, may be marked upon Luer-lock fitting 32 and Luer-lock connector 62, respectively, to ensure that specimen retaining notch 56 is properly aligned with cutting tip 22 of outer cannula 20 (see FIG. 5).

Referring now to FIG. 6C, biopsy needle 50 is shown inserted within outer cannula 20, and proximal end 28 of outer cannula 20 is shown being coupled with Luer-lock connector 62 of biopsy actuator 48. As shown in FIG. 6C, Luer-lock connector 62 is coupled by a control shaft 70 to the spring loaded mechanism within biopsy actuator housing 60. When coupling Luer-lock connector 62 to connector 32 at the proximal end 28 of outer cannula 20, the physician may grasp and stabilize handle 30 of outer cannula 20, while rotating biopsy actuator housing 60 one-quarter turn.

Prior to coupling Luer-lock connectors 62 and 32, thumb tabs 64 and 66 of biopsy actuator 48 are each retracted by the physician, and safety switch 70 is applied to prevent premature firing of biopsy actuator 48. Following insertion of biopsy needle 50 within outer cannula 20, and following the coupling of Luer-lock connectors 62 and 32, the relationship between distal tip 52 of biopsy needle 50 and distal tip 22 of outer cannula 20 is as shown in FIG. 6D. As shown, the specimen retaining notch 56 of biopsy needle 50 lies entirely within outer cannula 20. Upon releasing safety switch 70 and pulling back on trigger switch 68, biopsy actuator 48 initially advances biopsy needle 50 by a sufficient distance (approximately 20 millimeters) to completely expose specimen retaining notch 56 to the target tissue to be sampled, as shown in FIG. 6E, thereby permitting surrounding target tissue to prolapse within specimen retaining notch 56. Shortly thereafter, biopsy actuator 48 rapidly advances drive shaft 70 and Luer-lock connector 62 (see FIG. 6C) by a sufficient distance (approximately 20 millimeters) to cause the bevelled distal tip 22 of outer cannula 20 to slide across specimen retaining notch 56 to cut the tissue prolapsed within specimen retaining notch 56 and to once again cover specimen retaining notch 56, thereby capturing the tissue specimen therein.

The spring-loaded mechanism within biopsy actuator housing 60 that is used to sequentially advance biopsy needle 50 and Luer-lock connector 62 will not be disclosed in detail herein; such spring-loaded mechanism may be identical to that used within the above-described biopsy system that is commercially available from Boston Scientific Corporation under the "Meditech ASAP Biopsy System" trademark. Similarly, the energizing mechanism for the tissue sampling device disclosed in the aforementioned U.S. Pat. No. 4,699,154, issued to Lindgren may also be used to actuate biopsy needle 50 and Luer-lock connector 62 in timed sequence, and the disclosure of such patent is hereby incorporated by reference. Alternately, the biopsy needle may be fixedly secured to the biopsy actuator 48, and the spring-loaded mechanism may be configured to initially retract Luer-lock connector 62 to expose the distal tip of biopsy needle 50 and thereafter rapidly advance Luer-lock connector 62 to, in turn, rapidly advance the distal tip 22 of outer cannula 20 over distal tip 52 of biopsy needle 50. Such latter form of operation may be provided using the spring-loaded mechanism disclosed within the aforementioned U.S. Pat. No. 4,735,215 issued to Goto et al., the disclosure of which patent is hereby incorporated by reference.

As indicated above, the present invention also relates to the method of acquiring biopsy specimens using the apparatus generally described herein. Such method includes the step of inserting a stylet 34 within an outer cannula 20 through the proximal end 28 thereof to close the distal end 22 of the outer cannula. The method includes the further step of inserting the distal end 22 of the outer cannula, together with the stylet 34 disposed therein, into the patient's body 24 and directing the distal end 22 of the outer cannula 20 toward the target tissue mass 26 to be biopsied. The method includes the further step of removing stylet 34 from the outer cannula 20 after the distal end 22 of the outer cannula 20 lies closely proximate or within the target tissue mass 26.

The above-described method further includes the step of inserting into the proximal end 28 of outer cannula 20 a biopsy needle 50 extending from a biopsy actuator 48 until the distal tip 52 of the biopsy needle 50 is proximate the distal end 22 of outer cannula 20, with the specimen retaining notch 56 of biopsy needle 50 covered by outer cannula 20. The proximal end 28 of outer cannula 20 is then coupled to the biopsy actuator 48. The method includes the further step of triggering the biopsy actuator 48 to expose the specimen retaining notch 56 of biopsy needle 50 relative to the distal end 22 of outer cannula 20 for allowing surrounding tissue to prolapse therein, and to thereafter rapidly slide the distal end 22 of the outer cannula 20 over the specimen retaining notch 56 to cut the aforementioned prolapsed tissue and retain a tissue specimen therein. The method further includes the step of uncoupling the proximal end 28 of the outer cannula 20 from the biopsy actuator 48 and withdrawing the biopsy needle 50 from the proximal end 28 of the outer cannula 20 while outer cannula 20 remains within the patient to facilitate additional tissue biopsies from the same insertion tract.

The apparatus and method described herein provides a further advantage by allowing a physician to detect blood leakage paths which may have been created in performing the biopsy. Those biopsy systems already known in the art using mechanized trigger devices typically require that the outer cannula and the inner specimen-retaining biopsy needle be withdrawn concurrently. If the outer cannula and biopsy needle are withdrawn promptly to obtain the specimen, undetected blood leakage paths may exist. In contrast, use of the present apparatus and method permits the specimen retaining biopsy needle to be withdrawn quickly to obtain the specimen, while permitting the outer cannula to be withdrawn slowly. As the outer cannula is withdrawn, any blood leakage paths will be evidenced by blood flowing from the proximal end of the outer cannula. In such instances, corrective action (such as injecting autologous blood clot) may then be taken to ensure that such blood leakage paths are sealed before entirely removing the outer cannula.

Those skilled in the art will now appreciate that an improved apparatus and method for acquiring soft tissue biopsy specimens has been described which maintains the advantages of mechanized timed sequential actuation of the outer cannula and biopsy needle while still facilitating the use of CT guided scanning equipment or other imaging modalities to confirm proper placement of the cannula. Further, the described apparatus and method permits multiple specimens to be obtained without requiring multiple cannula placement procedures. While the invention has been described with reference to preferred embodiments thereof, the description is for illustrative purposes only and is not to be construed as limiting the scope of the invention. Various modifications and changes may be made by those skilled in the art without departing from the true spirit and scope of the invention as defined by the appended claims.

I claim:

1. A method for acquiring biopsy specimens of tissue from a patient, the method comprising the steps of:
   a) inserting a stylet into an outer cannula through a proximal end of the outer cannula to close a distal end of the outer cannula;
   b) inserting the distal end of the outer cannula, with the stylet disposed therein, into a patient while directing the distal end of the outer cannula toward a target tissue mass to be biopsied;
   c) removing the stylet from the outer cannula after the distal end of the outer cannula is proximate the target tissue mass;
   d) inserting into the proximal end of the outer cannula a biopsy needle extending from a biopsy actuator until a distal tip of the biopsy needle is proximate the distal end of the outer cannula, the biopsy needle having a specimen retaining notch proximate the distal end thereof;
   e) coupling the proximal end of the outer cannula to the biopsy actuator;
   f) triggering the biopsy actuator to expose the specimen retaining notch of the biopsy needle relative to the distal end of the outer cannula, and to subsequently slide the distal end of the outer cannula over the specimen retaining notch to retain a tissue specimen therein; and
   g) uncoupling the proximal end of the outer cannula from the biopsy actuator and withdrawing the biopsy needle from the proximal end of the outer cannula while the outer cannula remains inserted within the patient.

2. The method of claim 1 including the step of obtaining a second tissue specimen by temporarily leaving the outer cannula within the patient and repeating at least steps d) through f) of claim 8.

3. The method of claim 1 further comprising the step of obtaining at least one CT scan of the patient after step b) and before step d) to confirm proper placement of the distal end of the outer cannula relative to the tissue mass to be biopsied.

4. The method of claim 1 wherein said step of exposing the specimen retaining notch within the biopsy needle includes the step of advancing the distal tip of the biopsy needle beyond the distal end of the outer cannula to allow tissue proximate to the specimen retaining notch to prolapse therein, and wherein said step of sliding the distal end of the outer cannula over the specimen retaining notch cuts the tissue sample prolapsed within the specimen notch.

5. The method of claim 1 wherein said step of exposing the specimen retaining notch within the biopsy needle includes the step of retracting the distal end of the outer cannula to a point proximal of the specimen retaining notch while leaving the distal tip of the biopsy needle stationary for allowing tissue proximate to the specimen retaining notch to prolapse therein, and wherein the step of sliding the distal end of the outer cannula over the specimen retaining notch cuts the tissue sample prolapsed within the specimen notch.

* * * * *